United States Patent [19]
Bardsley et al.

[11] Patent Number: 5,708,011
[45] Date of Patent: Jan. 13, 1998

[54] USE OF LEVOBUPIVACAINE IN A PATIENT HAVING DEPRESSED MYOCARDIAL CONTRACTILITY

[75] Inventors: Hazel Judith Bardsley; Robert William Gristwood, both of Cambridge, United Kingdom

[73] Assignee: Chiroscience Limited, Cambridge, United Kingdom

[21] Appl. No.: 640,930

[22] PCT Filed: Oct. 13, 1994

[86] PCT No.: PCT/GB94/02249

§ 371 Date: Apr. 12, 1996

§ 102(e) Date: Apr. 12, 1996

[87] PCT Pub. No.: WO95/10277

PCT Pub. Date: Apr. 20, 1995

[30] Foreign Application Priority Data

Oct. 13, 1993 [GB] United Kingdom ............... 9321061
Apr. 22, 1994 [GB] United Kingdom ............... 9408014

[51] Int. Cl.$^6$ ............................................. A61K 31/445
[52] U.S. Cl. ............................................. 514/330
[58] Field of Search ............................................. 514/330

[56] References Cited

PUBLICATIONS

Valenzuela, C. et al. (1994) "Stereoselective Bupivacaine Block of the Human Cardiac Delayed Rectifier Kv1.5 Channel" Biophys. J. 66:A205, abstract No. Tu–Pos383.

Butterworth, J.F. et al. (1993) "Bupivacaine Inhibits Cyclic–3', 5'–Adenosine Monophosphate Production" Anesthesiology 79:88–95.

Clarkson, C.W., L.M. Hondeghem (1985) "Mechanism for Bupivacaine Depression of Cardiac Conduction: Fast Block of Sodium Channels during the Action Potential with Slow Recovery from Block during Diastole" Anesthesiology 62:396–405.

Courtney, K.R., J.J. Kendig (1988) "Bupivacaine is an effective potassium channel blocker in heart" Biochimica et Biophysica Acta 939:163–166.

Burm, A.G.L. et al. (1994) "Pharmacokinetics of the enantiomers of bupivacaine following intravenous administration of the racemate" Br. J. Clin. Pharmac. 38:125–129.

Vanhoutte et al, British Journal of Pharmacology, vol. 103, pp. 1275–1281 May 1991.

Rutten et al, British Journal of Anaesthesia, vol. 67, pp. 247–256 Sep. 1991.

*Primary Examiner*—William R.A. Jarvis
*Attorney, Agent, or Firm*—Saliwanchik, Lloyd & Saliwanchik

[57] ABSTRACT

This application relates to methods of using levobupivacaine substantially free of dexbupivacaine for anaesthetic treatment of pain in a patient having depressed myocardial contractility.

9 Claims, No Drawings

USE OF LEVOBUPIVACAINE IN A PATIENT HAVING DEPRESSED MYOCARDIAL CONTRACTILITY

This application is a 371 of PCT/GB94/02249, filed Oct. 13, 1994, published as WO95/10277 Apr. 20, 1995.

FIELD OF THE INVENTION

This invention relates to a new therapeutic use for a known analgesic agent, i.e. bupivacaine or 1-butyl-N-(2,6-dimethylphenyl)-2-piperidinecarboxamide.

BACKGROUND OF THE INVENTION

Racemic bupivacaine is an effective long-acting local anaesthetic, and may be given as an epidural. However, racemic bupivacaine is cardiotoxic, having depressant electrophysiological and mechanical effects on the heart. It should therefore be used with caution in cardiac-compromised patients.

It is known that levobupivacaine is probably less cardiotoxic than dexbupivacaine and racemic bupivacaine. See, for example, Vanhoutte et al, Br. J. Pharmacol. 103:1275–1281 (1991), and Denson et al, Regional Anaesthesia, 17:311–316 (1992). Vanhoutte et al studied the effects of bupivacaine enantiomers on the electrophysiological properties of guinea pig isolated papillary muscle; this is based on their statement that "the cardiotoxicity of bupivacaine seems to be mainly of electrophysiological origin".

Many patients who require analgesics are undergoing concomitant therapy with other drugs, e.g. anti-hypertensive agents. Many such drugs are cardio-depressant. In particular, it has recently been reported that cardio-depressant effects are observed in isolated organs, following administrations of bupivacaine and $Ca^{2+}$ channel inhibitors such as verapamil.

SUMMARY OF THE INVENTION

Surprisingly, it has been found that the effect of levobupivacaine on the heart is reduced, in respect not simply of electrophysiological properties, but also mechanical properties. Although racemic bupivacaine may have both electrophysiological and mechanical depressant effects on the heart, there is no evidence to suggest that these effects are linked.

In particular, it has now been found that levobupivacaine in man has less effect on stroke, cardiac and acceleration indices than racemic bupivacaine. As these are indices of myocardial contractility, this finding indicates that levobupivacaine is less cardio-depressant than racemic bupivacaine. This finding supports the use of levobupivacaine as a safer long-acting local anaesthetic for use in patients having or disposed to depressed myocardial contractility, i.e. a class of cardiac-comprised patients and also patients undergoing concomitant therapy with medicines having a cardio-depressant effect or with cytotoxic drugs. For the same reasons, levobupivacaine may also have beneficial therapeutic effects after certain kinds of surgery when sympathetic blockade is required with minimal cardio-depressant effects.

The agent may be the single isomer, but is effectively free of dexbupivacaine, e.g. in at least 80%, more preferably at least 90%, and most preferably at least 99%, enantiomeric excess. Any conventional salt, e.g. the hydrochloride, may be used.

DESCRIPTION OF THE INVENTION

For the purposes of the present invention, "depressed myocardial contractility" indicates that the patient is suffering from, or disposed to, heart failure at level 2, 3 or 4 of the New York Heart Association Scale. There are various therapeutic indications associated with reduced force of contraction of the heart, where the use of bupivacaine or its isomers, on the basis of prior knowledge, would have been contra-indicated. In certain populations, reduced mechanical effectiveness of the heart is a major problem.

Specific indications to which the present invention relates, and for which the use of levobupivacaine as an analgesic is thus appropriate, include hypertension, renal disease, viral illness, alcohol-dependence or effects, major ischaemia and diabetes. The invention is also applicable for providing anaesthesia in the old and frail, for stable post-infarct, shock, following cardiac surgery or multiple organ failure, and others at risk from post-myocardial infarcts.

The concentration of levobupivacaine to be given for effective utility, is for example, 0.25%, 0.5% or 0.75%, depending on the procedure envisaged. Up to 60 ml in a single dose can be given.. The usual routes of administration are infiltration, epidural, spinal and peripheral nerve block. It is also possible to provide continuous infusion of agent at lower concentration, for example 0.125%, with or without opioid, depending on anaesthetic practice. This is common during labour and is distinct from the treatment of chronic pain when infusions can continue for days rather than hours.

Art additional benefit of levobupivacaine over racemic bupivacaine is its reduced uptake into heart and brain. It is therefore particularly suitable for use in treating chronic pain. This is described more fully in the other International Patent Application filed today by Chiroscience Limited et al, with the same title, the contents of which are incorporated herein by reference.

The following provides the evidence that is the basis of the present invention.

The cardiovascular and central nervous effects of levobupivacaine were compared with racemate (Marcains) in healthy male volunteers. Drugs were administered by intravenous administration in a double-blind crossover manner. The infusion rate was 10 mg/min for each drug and infusion was continued up to a maximum of 150 mg or stopped following the first detection of CNS effects (including tinnitus, numb tongue or lips and dry mouth). Volunteers were previously conditioned to the CNS effects of local anaesthetics by administration of a test dose of lignocaine. A range of cardiovascular parameters were measured, including systolic and diastolic blood pressures, ECG, and, using the transthoracic electrical bioimpedance technique (with a BoMed NCCOM3-R7), aortic blood flow, allowing measurements of cardiac index and stroke index. Based on results from a previous study in which racemic bupivacaine was infused it was anticipated that the major cardiovascular changes observed following bupivacaine administration would be related to myocardial contractility. Therefore, an acceleration index, representing the initial maximum acceleration of blood flow during the onset of ejection, was measured to estimate myocardial contractility in this new study.

Levobupivacaine, like racemate, was well tolerated. The mean total doses administered of levobupivacaine and racemate were 54.0 and 45.6 mg respectively and plasma concentrations at the end of infusion were 2.384 µg/ml and 1.87 µg/ml respectively (n=12). Despite the mean total dose and plasma concentration being higher with levobupivacaine, this produced much smaller mean changes in cardiac variables than the racemate. The myocardial contractility index was significantly reduced by bupivacaine from a value of 1.36 $S^{-2}$ to 1.18 $S^{-2}$, a decrease of 0.18 $S^{-2}$ or 13%. For levobupivacaine the pre-dose value was 1.34 $S^{-2}$ and this only decreased to 1.28 $S^{-2}$ at the end of infusion, a decrease of 0.06 $S^{-2}$ or 4.5%. The difference between drug treatments was highly significant ($p<0.02$, $n=12$). The results were similar for stroke index, a parameter likely to reflect changes in myocardial contractility. Bupivacaine reduced this from 55.3 ml/$M^2$ to 44.4 ml/$M^2$, a decrease of 10.9 ml/$M^2$ or 20%. For levobupivacaine the pre-dose value was 52.4 ml/$M^2$ and 49.1 ml/$M^2$ at the end of infusion, a decrease of 3.3 ml/$M^2$ or 6%. Again the difference between drug treatments was statistically highly significant ($p<0.01$, $n=12$). Small changes in other variables occurred including heart rate and mean blood pressure (increases) and ejection fraction and cardiac index (decreases). As with acceleration index and stroke index the changes tended to be greater with bupivacaine.

A second study has been carried out, to compare the efficacy of levobupivacaine against bupivacaine using the ulnar block technique. Concentrations of 0.125%, 0.25% and 0.5% levobupivacaine were compared with 0.25% bupivacaine (all volumes 5 mls) in a double-blind study in 20 volunteers. A preliminary analysis of the data suggests that in terms of sensory block, levobupivacaine has comparable efficacy to bupivacaine, with the duration of sensory block to 0.25% bupivacaine being similar to that seen with levobupivacaine 0.25%.

These results with levobupivacaine have provided evidence that this local anaesthetic, in comparison with the currently clinically-used racemate, has a lower potential to cause cardiotoxicity in man. This, along with evidence that levobupivacaine has a similar anaesthetic potency to the racemate, suggests that levobupivacaine will be a safer local anaesthetic in the clinic. This would be of particular importance for obstetrics use and large plexus blocks where accidental intravenous injection of the racemate can have grave consequences. In addition, the lower propensity to cause myocardial depression would be beneficial in patients with compromised cardiac function.

Based on preclinical results obtained with separated enantiomers, the reduced cardiotoxicity of levobupivacaine in man is likely due to reduced direct actions on the heart. However additional factors may contribute to the reduced cardiotoxicity. Recently, others have reported stereoselective plasma binding of bupivacaine enantiomers in man, with the plasma binding of levobupivacaine being about 50% higher than binding for dexbupivacaine. This higher binding would reduce the consequences of accidental intravascular administration.

We claim:

1. A method for anaesthetic treatment of pain in a human patient having or disposed to having depressed myocardial contractility, said method comprising the administration of an effective amount of levobupivacaine or a salt thereof, to said patient, wherein said levobupivacaine is substantially free of dexbupivacaine.

2. The method, according to claim 1, wherein the patient is suffering from a condition selected from the group consisting of hypertension, renal disease, a post-myocardial infarct, ischaemia, diabetes, viral infection, and alcohol dependence.

3. The method according to claim 1, wherein the patient has undergone cardiac surgery, multiple organ failure or a valve replacement, or has been fitted with a pacemaker.

4. The method, according to claim 1, wherein the patient is undergoing concomitant therapy with a cardio-depressant drug.

5. The method, according to claim 1, wherein the patient is undergoing concomitant anti-hypertension therapy, by the administration of a $Ca^{2+}$ channel blocker.

6. The method, according to claim 1, wherein the patient is undergoing concomitant therapy with a cytotoxic drug.

7. The method, according to claim 1, wherein the levobupivacaine is in at least 90% enantiomeric excess with respect to dexbupivacaine.

8. The method, according to claim 5, wherein said $Ca^{2+}$ channel blocker comprises verapamil.

9. The method, according to claim 1, wherein the patient is suffering from, or disposed to, heart failure at level 2, 3, or 4 of the New York Heart Association Scale.

* * * * *